United States Patent [19]

Wurtman et al.

[11] Patent Number: 5,051,410

[45] Date of Patent: Sep. 24, 1991

[54] METHOD AND COMPOSITION FOR ENHANCING THE RELEASE OF NEUROTRANSMITTERS

[75] Inventors: Richard J. Wurtman, Boston; Jan K. Blusztajn, Cambridge, both of Mass.

[73] Assignee: Massachusetts Institute of Technology, Cambridge, Mass.

[21] Appl. No.: 239,542

[22] Filed: Sep. 1, 1988

[51] Int. Cl.$^5$ .......................................... A61K 31/685
[52] U.S. Cl. ....................................................... 514/78
[58] Field of Search .......................................... 514/78

[56] References Cited

U.S. PATENT DOCUMENTS 4,221,784  9/1980  Growdon et al. .
4,355,027  10/1982  Growdon et al. .

FOREIGN PATENT DOCUMENTS

89/03743  8/1989  PCT Int'l Appl. .

OTHER PUBLICATIONS

Ulus and Wurtman, *The New England Journal of Medicine*, 318: 191 (1988).
W. H. Kaye et al., In: Alzheimer's Disease: A Report of Progress, (*Aging*, vol. 19), S. Corkin et al., (eds.), pp: 433-442, Raven Press, New York, N.Y., (1982).
S. Bajada, In: *Alzheimer's Disease: A Report of Progress*, (*Aging*, vol. 19), S. Corkin et al., (eds.), pp. 427-732, Raven Press, New York, N.Y., (1982).
Peters and Levin, In: *Alzheimer's Disease: A Report of Progress*, (*Aging*, vol. 19), S. Corkin et al. (eds.), pp. 421-426, Raven Press, New York, N.Y., (1982).
*Advances in Alzheimer Therapy: Cholinesteriase Inhibitors, An International Symposium*, Mar. 1988.
Abstract No. 12, R. J. Wurtman et al., "Cholinesterse Inhibitors Increase the Brain's Need for Free Choline".
Abstract No. 19, S. Gauthier et al., "Tetrohydroaminoacridine and Lecithin in Alzheimer's Disease".
Maire and Wurtman, *J. Physiol.*, Paris, 80: 189-195 (1985).
Martin and Vyas, *British Journal of Pharmacology*, 90:561-565 (1987).
Martin, *Journal of International Medical Research*, 11:55-65 (1983).

*Primary Examiner*—Stanley J. Friedman
*Attorney, Agent, or Firm*—Hamilton, Brook, Smith & Reynolds

[57] ABSTRACT

Compositions useful in the treatment of neurological degenerative disorders which are characterized by reduced levels of acetylchone from neurons, as well as methods of use therefor are described. The compositions include pyritinol or a pyritinol derivative, analogue or metabolite, and choline or a source of choline.

11 Claims, No Drawings

METHOD AND COMPOSITION FOR ENHANCING THE RELEASE OF NEUROTRANSMITTERS

BACKGROUND

Exogenous choline is known to be required for acetylcholine (ACh) synthesis and to be supplied to cholinergic neurons, as choline or one of its precursors, from a variety of sources (e.g., circulation, breakdown of released ACh, efflux of free choline from the intra-cellular space of brain cells, hydrolysis of choline-containing membrane phospholipids). There are many diseases in which acetylcholine production and/or release appear to be affected. For example, Alzheimer's Disease is accompanied by a cholinergic defect in specific areas of the brain. A specific defect in choline acetyltransferase, the enzyme which catalyzes acetylcholine production from choline and acetyl-coenzyme A, has been identified in autopsy material from patients with Alzheimer's Disease. Summers, W. K. et al., *The New England Journal of Medicine*, 315:1241–1245 (1986) Davies, P. and Maloney, A. J. F., Lancet, 2:1403 (1976). Loss of cholinergic function is believed to contribute to the intellectual impairment, memory deficits and dementia which characterize Alzheimer's Disease. A. Enz, "Accumulation and Turnover of Ach After ACHE-I in Rat Brain", In: Advances in Alzheimer Therapy: Cholinesterase Inhibitors, An International Symposium, March 1988. Cholinergic deficiency states are also believed to be the basis for other neurological disorders. For example, it is thought that cholinergic deficiency states are present in such neurological disorders as Tourette's disease, Freidreich's ataxia, Huntington's Chorea amyelotrophic lateral scerosis, familiar dysautonomia, post-stroke, post-traumatic, or post-toxic syndromes affecting memory of cognition and tardive dyskinesia. S. Bajada, Alzheimer's Disease: A Report of Progress. In: *Aging*, S. Corkin, et al., (ed.) 9:427, Raven Press, New York, N.Y. (1982).

At least in part because of the evidence that a cholinergic defect (apparently low acetylcholine synthetic enzyme concentrations) is present in patients with Alzheimer's disease and that cholinergic mechanisms have a role in learning and memory, treatments have been devised in which choline or one of its precursors is administered in an attempt to counteract the acetyl choline deficiency. S. Bajada, Alzheimer's Disease: A Report of Progress. In: *Aging*, S. Corkin, et al., (ed.) 9:427 Raven Press, New York, NY (1982). Drugs which inhibit the action of cholinesterase, such as physostigmine and tetrahydroaminoacridine (THA), have also been used in treating Alzheimer's patients. Kaye et al., Alzheimer's Disease: A Report of Progress, In: *Aging*, S. Corkin, et al., (ed.) 9:433 Raven Press, New York, N.Y. (1982); Summers, et al., *New England Journal of Med.*, 315(20): 1241–1245 (1986). However, pharmacological therapy with cholinergic agents has had only limited success in patients with degenerative neurological disorders such as is evident in Alzheimer's Disease.

It would be useful to have a means by which the adverse effects of drugs administered to treat neurological diseases or conditions could be reversed or offset, with the result that the drug could have the desired therapeutic effect without impairing important activities, such as neuronal function.

SUMMARY OF THE INVENTION

This invention relates to a composition and process for the treatment of neurological degenerative disorders by enhancing acetylcholine levels in the brain without adversely affecting membrane phospholipid synthesis.

It is based on the discovery that the effect which the neurotropic drug pyritinol has been shown to have on intracellular choline metabolism can be countered or offset if supplemental choline is administered sufficiently closely in time to the pyritinol administration. That is, it has been shown that pyritinol enhances the synthesis and release of acetylcholine by neurons, that this enhancement is apparently the result of the shunting of intracellular choline from the choline kinase pathway to the choline acetyl transferase (CAT) pathway, and that cells can be protected against a possible effect of this shunting on membrane synthesis if supplemental choline is available to them. The choline kinase pathway is the route by which choline is converted, via a phosphocholine intermediate, to phosphatidylcholine, which is subsequently incorporated into membranes. Because pyritinol has the effect of "transferring" intracellular choline to the CAT pathway it also has the effect of reducing the availability of choline for phosphocholine synthesis and, thus, of phosphocholine for synthesis of an essential cell membrane component (phosphatidylcholine) and other phosphatides. Supplemental choline given with or close in time with pyritinol protects cells by ensuring that sufficient choline for phosphocholine (and thus, phosphatidylcholine) synthesis is available and that possible effects on membrane levels of phosphatidylcholine and other phosphatides are avoided. Depletion of membrane phospholipids is an undesirable theoretical side effect which could lead to impairment of neuronal function. The concomitant administration of choline, or a choline source or precursor, with the neurotropic drug prevents the depletion of membrane phospholipids.

The present combination provides distinct advantages in the treatment of diseases associated with decreased acetylcholine production and/or release. In particular, it means that the beneficial enhancement of production of acetylcholine by surviving neurons, which in effect, results in replacement of damaged neurons, can occur without concomitant depletion of membrane phospholipids which, if it occurred, would result in impaired neuronal function.

The composition of the present invention can be administered to an individual in an amount effective to substantially increase acetylcholine release by the neurons, to reduce the symptoms of the neurological disorder, and to not only avoid reduction in membrane levels of phosphocholine, but also maintain optical cell membrane phosphatidylcholine levels. In one embodiment of the present invention, a combination of choline or a precursor or source of choline, which is a precursor of acetylcholine and is a necessary component in membrane phospholipid synthesis, and pyritinol, which enhances acetylcholine production in neurons, is administered to an individual in a quantity sufficient to substantially increase the release of acetylcholine by the neurons while preventing depletion of phosphocholine and/or of membrane phospholipids. In one embodiment, choline (or a source thereof) sufficient to double blood choline levels in an individual is administered with an appropriate quantity of pyritinol.

Administration of choline or a choline source and pyritinol according to the method of the invention is beneficial to individuals suffering from neurological disorders, because it results in replacement or replenishment of acetylcholine lacking or not made/released by affected neurons, while avoiding the possible effects on phosphocholine synthesis which may result from administration of pyritinol alone.

DETAILED DESCRIPTION OF THE INVENTION

The invention relates to a composition to be administered to enhance the synthesis and release of acetylcholine from neurons and to maintain neuronal membrane phosphatidylcholine levels, as well as to a method of administering the composition to individuals for treatment of neurological disorders which are associated with decreased acetylcholine production.

The composition of the invention comprises choline or a choline source and pyritinol or a pyritinol derivative, analogue or metabolite. Choline itself can be used in the composition. Alternatively, a choline source, such as phosphatidylcholine, cytidyldiphospho choline, glycerophosphocholine or commercial lecithin, can be used. Pyritinol, which is also known as pyrithioxin; pyridoxine-5-disulfide; encefabol (or encephabol); bonifen; bonol; biocefalin; 3,3'-(Dithiodimethylene)-bis[5-hydroxy-6-methyl-4-pyridinemethanol]; bis(4-hydroxymethyl-5-hydroxy-6-methyl-3-pyridylmethyl)-disulfide; bis[(3-hydroxymethyl-2-methyl-5-pyridyl)methyl]disulfide; and dipyridoxolyldisulfide is also included in the composition. Pyritinol derivatives (which are compounds which have the same effect as pyritinol but have a modified chemical formula or are pyritinol analogues or metabolites) can also be included in the composition.

The choline and pyritinol can be administered orally, by subcutaneous or other injection, intravenously, parenterally, transdermally, rectally or via an implanted reservoir containing choline or a choline source and the neurotropic agent. The form in which the drugs will be administered (e.g. powder, tablet, capsule, solution, emulsion) will depend on the route by which it is administered. The quantity of the drugs to be administered will be determined on an individual basis, and will be based at least in part on consideration of the individual's size, the severity of the symptoms to be treated and the result sought.

In general, quantities of choline or a choline source sufficient to double blood choline levels will be administered. (Blood choline levels generally range from 7-9 nanomoles/ml.) For example, approximately 6-9 gm. of pure phosphatidylcholine a day (given in one dose or a number of smaller doses) will be adequate in most individuals to produce the desired doubling. In general, 3-100 gm. of phosphatidylcholine will be given in conjunction with pyritinol. Normally, lecithin is not available in pure form and is available as a mixture of lecithin and other phospholipids; typically 20-30 weight percent of such mixtures is lecithin. Mixtures such as these in which lecithin is one component are referred to as commercial lecithin.

The composition of the present invention can optionally include, in addition to choline or a choline source and pyritinol, other components. The components included in a particular composition are determined primarily by the manner in which the composition is to be administered. For example, a composition to be administered orally in tablet form can include, in addition to the drugs, a filler (e.g. lactose), a binder (e.g. carboxymethyl cellulose, gum arabic, gelatin), an adjuvant, a flavoring agent, a coloring agent and a coating material (e.g. wax or a plasticizer). A composition to be administered in liquid form can include the combination of drugs of the present invention, and, optionally, an emulsifying agent, a flavoring agent and/or a coloring agent.

In general, the composition of the present invention is administered to an individual periodically as necessary to improve symptoms of the disease being treated. The length of time during which it is administered and the dosage will depend on the disease being treated, the type and severity of the symptoms, and the physical condition of the individual being treated.

It is also possible to administer the choline and the pyritinol separately (i.e., not as two components of a single composition), provided that they are administered sufficiently closely in time (e.g., within the same day or 24-hour period) for the choline to be available as needed by cells for phosphocholine synthesis.

The composition of the present invention can be used to treat neurological disorders which are characterized by degeneration of cholinergic neurons or other neurological disorders which cause deficiencies in acetylcholine release. Such diseases include Alzheimer's disease, post-polio syndrome, myasthenia gravis, Huntington's disease, age-related memory disorders, post-traumatic, post-stroke or post-toxic syndromes affecting memory or cognition, dysautonomia or any other disorder affecting memory or cognition.

The acetylcholine-enhancing neurotropic agent pyritinol enhances the release of acetylcholine. However, it also negatively affects phosphocholine synthesis, and can thereby influence membrane phosphatidylcholine. A reduction in membrane levels of phosphatidylcholine and other phosphatides would very likely impair neuronal function (e.g., synaptic remodeling in learning), and even neural cell survival. Administration of supplemental choline results in protection of neurons against depletion of phosphocholine. The choline source can also provide a source of free choline. The availability of extracellular choline can influence the synthesis and release of acetylcholine, the synthesis of phophatidylcholine and levels of phosphatidylcholine in membranes. When extracellular choline is inadequate, choline in membrane phosphatidylcholine can be mobilized to serve as a precursor for acetylcholine synthesis. This can be problematic, however, because neuron membrane phospholipids can be depleted. This depletion can be reduced by supplying choline to the neurons. Ulus and Wurtman, *The New England Journal of Medicine*, 318(3):191 (1988).

The combination of pyritinol with choline results in a potentiation of the release of acetylcholine without the corresponding reduction of membrane phopholipids which occurs with pyritinol alone. The synergistic effect of the combination will be useful in treating Alzheimer's disease and/or other neurological disorders involving reduced acetylcholine production.

The invention is illustrated by the following exemplification, which is not to be seen as limiting in any way.

EXEMPLIFICATION

Effects of Pyritinol on Acetylcholine Synthesis and Release in Human Neuroblastoma Cells

Materials and Methods

Cell Culture

LA-N-2 cells (passage 70-90) which synthesize and release large amounts of acetylcholine (ACh) (J. K. Blusztajn et al., 1987, Proc. Nat'l. Acad. Sci., 84:5474-5477) were maintained in L15 medium, supplemented with 10% fetal calf serum and 100 uM choline chloride, in humidified room air at 37° C. Medium was changed twice weekly. Cells were subcultured at subconfluent density by brief (90 s) exposure to a solution of 0.1% viokase (Viobin Co. Monticello, Ill.) in phosphate buffered saline.

Acetylcholine Synthesis and Release

Choline uptake and metabolism were studied in cells incubated in the presence of [$^{14}$C-methyl] choline. The cells were grown on 35 mm dishes in 2 ml of L15 medium (as above) until nearly confluent. They were then grown for 24 hours in 2 ml of serum-free N2 medium (the lack of serum causes morphological differentiation, i.e., neurite formation) containing 10 uM choline and various concentrations of pyritinol, as indicated. The cells were labeled with [$^{14}$C] choline for one hour at 37° C. in Hanks Balanced Salt Solution (containing in mM: NaCl, 118; KCl, 5; CaCl$_2$, 1; and glucose, %), buffered at pH 7.6 with 15 mM HEPES and containing 60 uM eserine (HBSS) and pyritinol as indicated. The labeling media were aspirated, the dishes washed with HBSS and 1 ml of fresh HBSS was added to the dishes. Experimental incubations were for 30 min at 37° C. The test agents (potassium, pyritinol were added as indicated).

At the end of the incubation period, media from quadruplicate dishes were applied to columns of silicic acid (BioSil) A, Bio Rad Co., Richmond, Calif.) and chromatographically fractionated as follows: an aqueous slurry of silicic acid was added to glass-wool plugged disposable pasteur pipettes to a height of 8 mm. The columns were washed with 2 ml of water and after application of samples, washed successively with 1 ml of 0.001M HCl. The adsorbed choline and ACh were eluted with 0.8 ml 0.075M HCl and 0.75 ml 0.03M HCl in 10% methyl ethyl ketone into conical microtubes and dried under a vacuum. The treatment removes the salts present in HBSS and allows further purification of choline and ACh on HPLC (see below). One ml of methanol was added to the dishes, the cells were scraped off the dishes, and the methanolic suspensions were transferred to polypropylene tubes and vortexed vigorously. Two ml of chloroform were added, followed by 1 ml of water, and the mixtures were again vortexed. The phases were separated by centrifugation for 5 min at 800× g and the upper (aqueous) phase was collected and dried under a vacuum. The water-soluble metabolites of [$^{14}$C] choline were purified by a modification of a previously described HPLC procedure. The residues of media or cell extracts were reconstituted in 120 ul of water, filtered, and 100 ul aliquots subjected to HPLC.

Results

1. Effect of pretreatment with pyritinol on acetylcholine synthesis and release

In most experiments pyritinol caused elevation in ACh release. The elevation of potassium-evoked release was larger than that of spontaneous release (Table 1).

TABLE 1

| Effect of Pyritinol on [$^{14}$C] Acetylcholine Release From LA-N-2 Cells | | |
|---|---|---|
| | [$^{14}$] acetylcholine (dpm/dish) | |
| | 5 mM K$^+$ | 50 mM K$^+$ |
| control | 508 ± 113 (5) | 775 ± 158 (5) |
| pyritinol | 520 ± 192 (4) | 1447 ± 410 (4) |

La-N-2 cells were incubated for 24 hours in serum-free N2 medium containing pyritinol (100 uM), where indicated. They were labeled for one hour with [$^{14}$C] choline at concentrations indicated, followed by a 30 minute period without the label in Hank's balanced salt solution containing 5 mM or 50 mM potassium as indicated. The results are means ±SD (n).

2. Effect of pyritinol on phosphocholine synthesis

Pyritinol also caused a marked inhibition of [$^{14}$C]choline incorporation into phosphocholine. When extracellular choline was elevated from 8.5 uM to 60 uM, this inhibition was blunted and the actual amounts of intracellular phosphocholine returned to levels observed at 8.5 uM extracellular choline (Table 2).

TABLE 2

| Effect of Pyritinol and Choline on [$^{14}$C] phosphocholine in LA-N-2 Cells | | |
|---|---|---|
| | [$^{14}$] phosphocholine (pmol/dish) | |
| | Control | Pyritinol |
| 8.5 uM choline | 144 ± 36 (7) | 50 ± 24 (6) |
| 60.0 uM choline | 244 ± 133 (6) | 108 ± 38 (4) |

LA-N-2 cells were incubated for 24 hours in serum-free N2 medium containing pyritinol (300 uM), where indicated. They were labeled for one hour with [$^{14}$C]choline at concentrations indicated, followed by a 30 minute period without the label. [$^{14}$C]phosphocholine was purified and its amounts calculated using the specific radioactivity of the extracellular choline precursor. The results are means ±SD (n).

Conclusion

It was concluded that acute treatment with pyritinol does not result in changes of choline turnover. Pyritinol decreases phosphocholine synthesis by inhibiting the phosphorylation of choline in cells treated for 24 hours. Additional choline protects cells against this effect of pyritinol.

Pyritinol increases depolarization ACh release.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A composition for treatment of a neurological disorder, comprising choline or a choline precursor in an amount sufficient to increase blood choline levels in the individual up to about 18 nm/ml and pyritinol.

2. A composition of claim 1 wherein the choline precursor is selected from the group consisting of: phosphatidylcholine, glycerophosphocholine lecithin and cytidyldiphosphocholine.

3. A composition of claim 2 additionally comprising a binder and a filler.

4. A composition for administration to an individual having a neurological disorder in which acetycholine production by neurons is reduced, comprising choline or a choline precursor and pyritinol.

5. A method of treating a neurological disorder in which cholinergic neurons are affected, comprising administering to an individual an amount of choline or a choline precursor sufficient to increase blood choline levels in the individual up to about 18 nm/ml and an effective quantity of pyritinol.

6. A method of claim 5 wherein the choline precursor is selected from the group consisting of: phosphatidycholine, glycerophosphocholine lecithin and cytidyldiphosphocholine.

7. A composition for treating a neurological disorder in which cholinergic neurons are affected, comprising choline in an amount sufficient to increase blood choline levels in the individual up to about 18 nm/ml and pyritinol.

8. A method of treating a neurological disorder in which cholinergic neurons are affected comprising administering to a person having such a neurological disorder an amount of choline sufficient to raise blood choline levels up to about 18 nm/ml and pyritinol.

9. A composition of claim 1 wherein the choline precursor is selected from the group consisting of: phosphatidylcholine, glycerophosphocholine, lecithin and cytidyldiphosphocholine.

10. A method for enhancing the release of acetylcholine from neurons comprising administering to a person an amount of choline or a choline precursor sufficient to raise blood choline levels up to about 18 nm/ml and an effective amount of pyritinol.

11. A method of claim 10, wherein the choline source is selected from the group consisting of phosphatidylcholine, glycerophosphocholine, lecithin and cytidyldiphosphocholine.

* * * * *

UNITED STATES PATENT AND TRADEMARK OFFICE
CERTIFICATE OF CORRECTION

PATENT NO. : 5,051,410

DATED : September 24, 1991

INVENTOR(S) : Richard J. Wurtman and Jan Kyzysztof Blusztajn

It is certified that error appears in the above-identified patent and that said Letters Patent is hereby corrected as shown below:

Claim 2, Column 7, line 3, insert a comma after the word "glycerophosphocholine".

Claim 6, Column 7, line 19, insert a comma after the word "glycerophosphocholine".

Claim 6, Column 7, line 18, delete "phosphatidycholine" and insert ---phosphatidylcholine---.

Signed and Sealed this

Second Day of March, 1993

Attest:

STEPHEN G. KUNIN

Attesting Officer

Acting Commissioner of Patents and Trademarks